United States Patent [19]

Lecoffre

[11] Patent Number: 4,644,808
[45] Date of Patent: Feb. 24, 1987

[54] APPARATUS FOR MEASURING THE CONCENTRATION OF CAVITATION NUCLEI IN A LIQUID

[75] Inventor: Yves Lecoffre, Le Versoud, France

[73] Assignee: Alsthom, France

[21] Appl. No.: 807,081

[22] Filed: Dec. 10, 1985

[30] Foreign Application Priority Data

Dec. 10, 1984 [FR] France ............................... 84 18820

[51] Int. Cl.$^4$ ............................................. G01M 10/00
[52] U.S. Cl. ......................................... 73/866; 73/148
[58] Field of Search ............................ 73/148, 86, 866

[56] References Cited

U.S. PATENT DOCUMENTS 4,058,004 11/1977 Hammitt et al. ......................... 73/86
4,084,432 4/1978 Lecoffre ................................. 73/148

FOREIGN PATENT DOCUMENTS 384021 8/1973 U.S.S.R. ................................. 73/86
0823938 4/1981 U.S.S.R. ............................... 73/148

OTHER PUBLICATIONS

Journal of Physics E. Scientific Instruments, vol. 15, No. 7, Jul. 1982, pp. 741–745, The Institute of Physics, London, GB M. K. De et al, "Instrument System for Monitoring Cavitation Noise".

ISA Transactions, vol. 22, No. 3, 1983, pp. 71–80, ISA, Research Triangle Park, U.S.: M. L. Riveland, "The Industrial Detection and Evaluation of Control Valve Cavitation".

*Primary Examiner*—Michael J. Tokar
*Assistant Examiner*—Robert R. Raevis
*Attorney, Agent, or Firm*—Sughrue, Mion, Zinn, Macpeak and Seas

[57] ABSTRACT

In hydrodynamic testing, in particular in laboratory testing of propellers, it is necessary to measure the concentration of cavitation nulcei in a liquid. The measurement is performed by counting bubbles of vapor formed by the cavitation nuclei in a zone (C) having minimum cross-section and pressure (Pt) in a forced flow along a duct. A deflector core (18) is disposed on the axis of a diverging downstream portion (C) of said duct in order to avoid the liquid streamlines from becoming detached and to facilitate bubble counting.

7 Claims, 4 Drawing Figures

U.S. Patent   Feb. 24, 1987   4,644,808
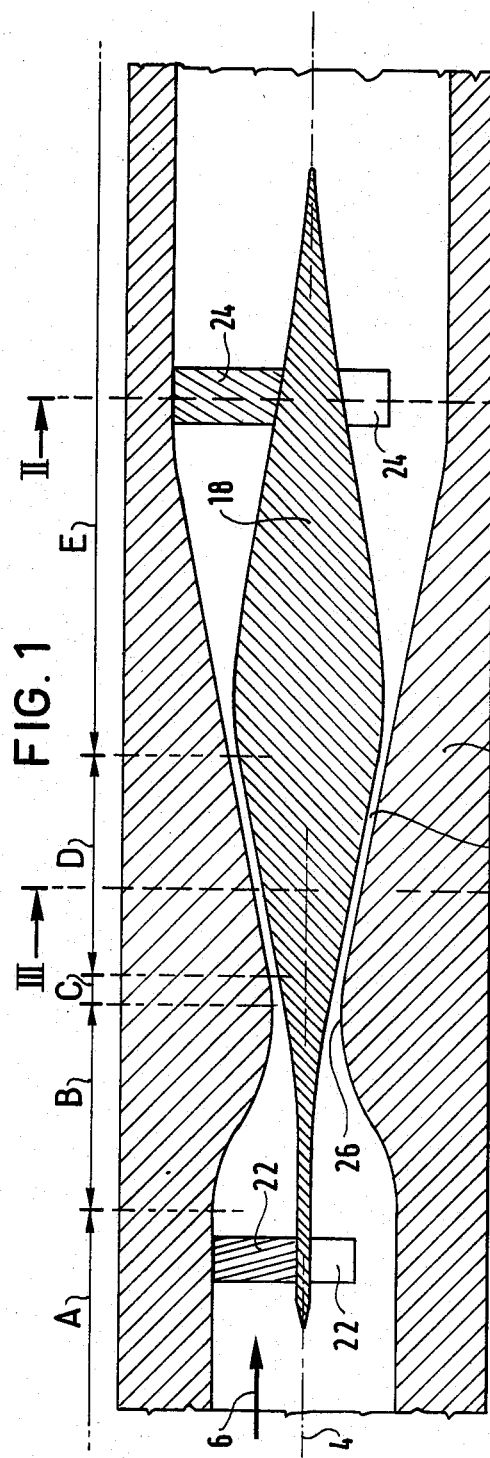
FIG. 1
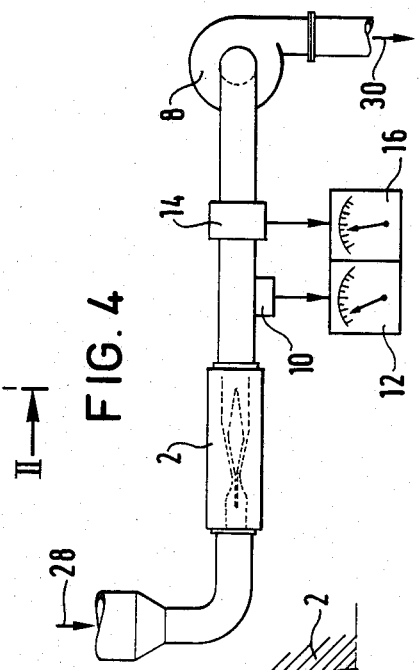
FIG. 4
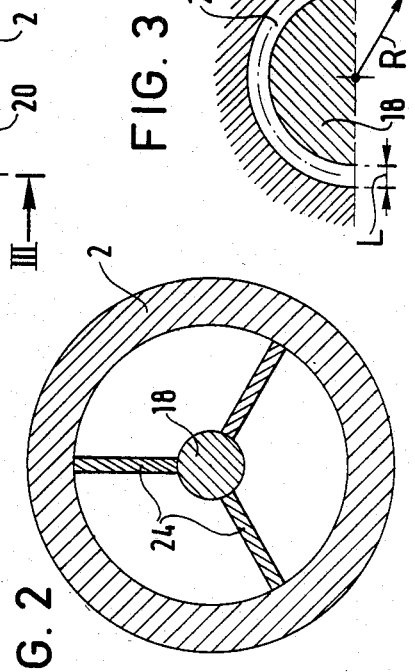
FIG. 3
FIG. 2

APPARATUS FOR MEASURING THE CONCENTRATION OF CAVITATION NUCLEI IN A LIQUID

BACKGROUND OF THE INVENTION

In hydrodynamics, liquid flows are encountered which are referred to as being "cavitating" because a local pressure drop may give rise to bubbles of vapor which may suddenly disappear by implosion due to a subsequent rise in pressure or which may attach themselves to a solid wall and grow in volume, thus forming a cavity. Cavitation, i.e. the appearance of such bubles, is an important phenomenon: for example it is cavitation which oftens limits the maximum propulsive power of a ship's propeller.

The behavior of cavitating flows is highly influenced by the concentration of nuclei in the liquids which constitute such flows. These nuclei are weak points in the structure of said liquids. They may be of known or unknown nature, but in practice they may always be measured in terms of their critical pressures. That is to say by that pressure which is less than the vapor pressure and is often negative, to which the liquid surrounding a nucleus must be subjected in order to give rise to a bubble of vapor.

In several practical situations, for example when testing a propeller in a laboratory, it is necessary to be able to measure the concentration of such nuclei at various critical pressures in the liquids being used. This concentration of cavitation nuclei is generally shown in the form of a histogram showing a cumulative concentration as a function of decreasing critical pressure.

The present invention enables such measurements to be performed.

The concentration of nuclei in a liquid is currently measured using two types of method: there are so-called "non-cavitating" methods which are used when the nature of the nuclei is known. The nuclei are generally micro-bubbles in this case. A magnitude is measured representative of their size. A transposition formula is used to deduce the critical pressure therefrom. Such methods include: holography, Coulter's electrical method, and the light diffusion method.

In so-called "cavitating" methods, the liquid is forced to pass at high speed through a venturi (i.e. a Venturi tube). A conventional venturi comprises a converging portion leading to a throat and followed by a diverging portion, the flow cross-section is circular throughout and the minimum diameter is at the throat.

A region of minimum adjustable pressure Pt is thus created at the throat of the tube, which pressure may be less than the vapor pressure of the liquid. When a nucleus passes through the tube it may be excited or it may not depending on whether its critical pressure Ps is greater than or less than the pressure Pt. The pressure Pt may be varied by varying the water flow rate passing through the venturi, and classes of nuclei having different critical pressures can thus be excited, thereby enabling the histogram representative of the nucleus population to be determined, by detecting and counting excited nuclei and by measuring the pressure Pt and the water flow rate. Such cavitating methods are described in particular in the following documents:

O.N.R. Symposium, Ann Arbor University (Michigan) 1981, in a communication by Y. Lecoffre and J. P. Legoff (Nuclei and cavitation); and A.I.R.H. Bulletin, Amsterdam 1982 "Aspects pratique du contrôle de germes de cavitation en moyens d'essais" by Lecoffre, Marcoz, Valibouze, (Practical aspects of monitoring cavitation nuclei in test equipment).

Apparatus in accordance with the present invention uses a cavitating method.

Presently existing apparatuses using such a method suffer, at present, from three major defects:

1. There is a high degree of interaction between the bubbles developing in the venturi throat and the incident flow. Thus, at a given water flowrate, the throat pressure varies as a function of time and the accuracy of the measurements is poor, in particular when the concentration of active nuclei is high or when the pressure Pt is very low;

2. Measurable concentrations are limited to a few nuclei per $cm^3$, which is insufficient in some applications; and 3. Venturi tubes are difficult to make and their reliability can pose serious problems. More precisely, their surface state must be excellent in order to obtain reliable measures, and this requires sophisticated and expensive machining methods to be used such as certain kinds of mechanical and electrolytic polishing.

The aim of the present invention is to provide apparatus for measuring the concentration of cavitation nuclei in a liquid in such a manner as to obtain accurate and reliable measurements at low cost even when the concentration of nuclei is high.

SUMMARY OF THE INVENTION

The invention provides apparatus for measuring the concentration of cavitation nuclei in a liquid, said apparatus comprising:

a pressure-reducing duct (2) for said liquid, said duct having a length and an axis (4) along the flow direction (6) and comprising an upstream portion (B) in which the cross-section of the liquid decreases up to a zone (C) of substantially minimum flow cross-section and of predetermined length, and a downstream portion (D,E) in which the liquid flow cross-section increases progressively from said minimum cross-section;

circulation means (8) for causing said liquid to flow along said duct at a sufficient rate to ensure that the liquid locally reaches a predetermined minimum pressure (Pt) in said minimum section zone (C), which minimum pressure is sufficiently low to ensure that the cavitation nuclei under consideration, i.e. those nuclei whose concentration in the liquid is to be measured, give rise to bubbles of vapor of sufficient individual volume for them to be detected individually;

means (10) for detecting the bubbles created in this way;

means (12) for counting the bubbles detected in this way, to measure the number thereof in a given period of time: and means (14, 16) for obtaining the flowrate of the liquid flowing along the duct in such a manner as to enable the concentration to be measured to be deduced from said number of bubbles and said flowrate:

wherein said pressure-reducing duct (2) includes a deflector core (18) disposed along the axis (4) of the duct and extending at least over a part of the downstream portion (D, E) thereof in such a manner that the cross-section of the liquid is constituted over the length of said core by an annular passage (20) between said core and said tube so that a spherical bubble can occupy only a small fraction of the liquid cross-section, each right cross-section through the duct and said annular passage showing the passage to have radial widths (L) extending in directions going away from the axis of the duct, and an average circumferential length ($2\pi R$) which is the length of the line which connects the middles of its widths wherein R is the average radius of said annular passage.

Naturally the bubbles which are likely to be formed are not necessarily exactly spherical in shape, however they are close to being spherical.

The reference signs between parentheses refer, by way of example, to the figures.

Such a configuration provides a convergent-divergent flow having the advantageous characteristics of the known type of flow through a venturi, i.e. a reduction in pressure followed by an increase in pressure. However, it also has the essential advantage that the pressure rise takes place without any risk of the boundary layer becoming detached (which phenomenon, when it occurs, completely disturbs the operation of the apparatus), and this remains true even when the apparatus is manufactured by conventional machining techniques. Fine machining techniques should naturally be used, but there is no need to take special precautions.

Further, the width of the annular passage may be tailored in such a way that interactions between cavitation bubbles and the incident flow is very low. By virtue of said limited width, several bubbles may grow simultaneously in the annular space, thereby enabling high counting rates to be achieved.

In accordance with the present invention it has also appeared advantageous to adopt, at least in some cases, the following more specific arrangements:

the cross-sections of said detector core (18) and of the duct (2) around said core are substantially circular and concentric, the radius of the core section being equal to not less than 70% of the inside radius of the surrounding duct, over at least a part of the length of said core in such a manner as to limit the maximum possible diameter of a spherical bubble in said downstream portion;

said deflector core (18) and the surrounding duct (2), at least over a part (D) of said downstream portion (D, E), have the shape of two coaxial and substantially conical surfaces whose diameters increase in the downstream direction, whereby said increase in passage section in the downstream direction results at least partially from the increase in said circumferential length of the annular passage (20), and it preferably results mostly or completely therefrom, with said radial width remaining constant;

the inclination of the duct (2) constituted by the halfangle at the apex of said conical duct surface lies between 0° and 45° in at least an upstream part (D) of said downstream portion (D, E), the inclination of said deflector core (18) constituted by the half-angle at the apex of said conical core surface being a function of the inclination chosen for the duct;

the inclination of said deflector core (18) and the surrounding duct (2) change smoothly going away from said conical surfaces in order to avoid disturbing the flow of said liquid; and said means for detecting bubbles of vapor are acoustic means (10) for detecting bubble implosions in said annular passage gap (20), said means being disposed downstream and at a distance from said zone of minimum section (C).

BRIEF DESCRIPTION OF THE DRAWING

An implementation of the invention is described below by way of non-limiting example and with reference to the accompanying diagrammatic figures. When the same item is shown in several figures, it is designated throughout by the same reference symbol.

FIG. 1 is a section through a pressure-reducing duct in apparatus in accordance with the invention, the section being on a plane including the axis of the duct.

FIG. 2 is a cross-section through the same duct on a plane II—II of FIG. 1, said plane being perpendicular to the axis of the duct.

FIG. 3 is a half-section through the same duct to an enlarged scale and on a plane III—III of FIG. 1, said plane being perpendicular to the axis of the duct.

FIG. 4 is an overall view of apparatus in accordance with the invention and including said duct.

MORE DETAILED DESCRIPTION

The measuring apparatus shown includes the above-mentioned dispositions in accordance with the invention. In this apparatus said pressure-reducing duct 2 is circularly symmetrical about its axis 4 and includes various portions which are enumerated below along the direction of water flow, where said liquid is constituted by water, said direction being represented by an arrow 6. These portions are:

An inlet portion A in which the liquid flow cross-section is circular and substantially constant, with spacers 22 occupying negligible volume.

Said upstream portion B of decreasing cross-section.

Said zone C of substantially constant minimum cross-section and of substantially minimum pressure, in which some of the nuclei give rise of bubbles of vapor. These nuclei are those whose critical pressure Ps is greater than or equal to the reduced pressure Pt created in said zone by the water being accelerated. Those of the nuclei which have a critical pressure that is considerably greater than said minimum pressure Pt give rise to such bubbles in the upstream portion B. These bubbles grow rapidly in volume in said zone.

Said downstream portion D in which the cross-section of the passage increases and the pressure rises. Some bubbles may continue to grow in volume in the upstream part of this portion, but the effect of the rising pressure is to cause all of the bubbles to implode suddenly before leaving this portion. Each bubble implosion creates a shock wave which propagates through the water and into the wall of the tube.

An outlet portion E in which the passage cross-section increases further without bubbles and which serves to facilitate establishing a flow of water downstream from the apparatus.

Said deflector core 18 is held along the axis 4 of the pressure-reducing duct 2 by two groups of three streamlined radial spacers, one group of spacers 22 being located in the inlet portion A of the duct and the other group of spacers 24 being located in the outlet portion E. This support serves to prevent the core 18 from vibrating. As shown, the presence of the core can ensure that the minimum flow cross-section is reached downstream from the throat 26 of the venturi which would be constituted by the duct 2 in the absence of its core. This flow section is equal to the circumferential length $2\pi R$ of the annular passage 20 multiplied by its radial width L, with the average radius R and the width L of said gap being shown in FIG. 3.

The beneficial effects of the core being present seem to stem from the following facts:

The core deflects the liquid streamlines radially outwardly prior to the liquid reaching the minimum pressure zone, thereby tending to avoid said streamlines becoming detached.

The fact that the liquid streamlines are parallel to the walls in the downstream portion avoids the bubbles attaching themselves to said walls.

The small width of the annular passage 20 limits the speed at which the largest bubbles can grow. Firstly this reduces the probability of two bubbles originating from different nuclei combining to form a single bubble. Secondly this limits the energy of the shock waves created further downstream by the largest bubbles imploding, thereby facilitating detection of the implosions due to smaller bubbles.

Further, this energy limitation reduces the risk of shock waves created by the implosions of the largest bubbles from propagating upstream and causing bubbles to appear without nuclei in the minimum section zone.

In FIG. 4, arrows 28 and 30 represent the inlet and the outlet for the water being investigated, said circulation means are constituted by a pump 8 which is shown symbolically, said detection means are constituted by an acoustic bubble detector 10 connected to a bubble counter 12, said means for measuring the liquid flowrate are constituted by a flowrate measuring apparatus 14 associated with a display 16, and all these means are placed downstream from the pressure-reducing duct 2. Counter 12 counts the number of bubbles passing by bubble detector 10, over a given time period.

The duct is made of metal, e.g. polished brass. However, it could be made of a rigid transparent material such as a polymethyl methacrylate in the event that said detection means were optical in nature and detected light diffused by the bubbles.

Other known materials could be used in other cases, for example when the concentration of nuclei is to be measured in a molten metal.

The bubbles could be detected by electrical methods, etc..

In the embodiment described, the following numerical values may be applied:
water flowrate: 1 liter per second
diameter of inlet portion A: 20 mm
length of upstream converging portion B: 15 mm
diameter of apparent throat 26 in duct 2: 10 mm
half-angle at the apex of the two cones: 20°
average width of the gap between these two cones: 1 mm
length of the minimum section zone C: 1 5 mm
length of the downstream portion D: 25 mm These various numerical values give a minimum pressure Pt a negative value of about −5 bars when the pressure in the inlet portion A is equal to 5 bars. Increasing the flowrate naturally gives rise to a corresponding decrease in this minimum pressure.

I claim:

1. Apparatus for measuring the concentration of cavitation nuclei in a flowing liquid, said apparatus comprising:

a pressure-reducing duct for confining flow of said liquid during passage of liquid in a given flow direction through said duct, said duct having a length and an axis along the flow direction and comprising a venturi passage including an upstream portion having a flow cross-section of the liquid which decreases up to minimum flow cross-section so as to progressively decrease the pressure, a minimum pressure portion having a predetermined length, and a downstream portion having a flow cross-section which increases progressively so as to increase the pressure;

circulation means for causing said liquid to flow through said duct venturi passage at a sufficient rate to ensure that the pressure in said minimum pressure portion is sufficiently low to ensure that the cavitation nuclei whose concentration in the liquid is to be measured, give rise to bubbles of vapor of sufficient individual bubble volume to be detected individually;

means for detecting the bubbles created in this way;

means for counting the bubbles to measure the number of bubbles in a given period of time; and means for obtaining the flowrate of the liquid flow through the duct venturi passage in such a manner as to enable the nuclei concentration to be deduced from said number of bubbles and said flow rate:

the improvement wherein said duct is made of an outer tube and of an inner coaxial core and the said venturi passage flow cross-section of the liquid is constituted over the length of said core by an annular passage between said core and said tube so that a spherical bubble can occupy only a small fraction of the liquid cross-section, each right cross-section through the duct and said annular passage showing the passage to have a radial widths extending in directions going away from the axis of the duct, and an average circumferential length which is the length of the line which connects the middles of its widths.

2. Apparatus according to claim 1, wherein the cross-sections of said core and of the duct around said core are substantially circular and concentric, the radius of the core section being equal to not less than 70% of the inside radius of the surrounding duct, over at least a part of the length of said core in such a manner as to limit the maximum possible diameter of said spherical bubble in said downstream portion.

3. Apparatus according to claim 1, wherein said core and the surrounding duct, at least over a part of said downstream portion, have the shape of two coaxial and substantially conical surfaces whose diameters increase in the downstream direction and wherein an increase in passage cross-section in the downstream direction occurs, with said increase at least partially resulting from an increase in the circumferential length of the annular passage.

4. Apparatus according to claim 3, wherein the majority of said increase of said passage cross-section results from said increase in circumferential length.

5. Apparatus according to claim 4, wherein the inclination of the duct as constituted by the half-angle at the apex of said conical duct surface lies between 0° and 45° in at least an upstream part of said downstream portion.

6. Apparatus according to claim 4, wherein the inclination of said core and the surrounding duct change smoothly going away from said conical surfaces in order to avoid disturbing the flow of said liquid.

7. Apparatus according to claim 1, wherein said means for detecting bubbles of vapor are acoustic means for detecting bubble implosions in said annular passage, said means being disposed downstream and at a distance from said venturi passage portion of minimum pressure.

* * * * *